US00PP32288P2

(12) United States Plant Patent
Hansen

(10) Patent No.: US PP32,288 P2
(45) Date of Patent: Oct. 6, 2020

(54) ***PHLOX* PLANT NAMED 'ROCKY ROAD VIOLET BLUE'**

(50) Latin Name: ***Phlox* hybrid**
Varietal Denomination: Rocky Road Violet Blue

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/873,083

(22) Filed: Jan. 30, 2020

(51) Int. Cl.
*A01H 6/70* (2018.01)
*A01H 5/02* (2018.01)

(52) U.S. Cl.
USPC ..... Plt./320

(58) Field of Classification Search
USPC ..... Plt./320
CPC ..... A01H 6/70; A01H 5/02
See application file for complete search history.

*Primary Examiner* — Annette H Para

(57) ABSTRACT

A unique cultivar of Hybrid Creeping *Phlox* named 'Rocky Road Violet Blue' characterized by vigorous, dense, spreading, multi-stemmed, winter-hardy habit with short, bright glossy-green, linear leaves. Flowering begins in mid-April and continuing for up to five weeks, in cooler weather conditions, on heavily-branched peduncles and completely cover the plant in peak season. Petals of newly opened flowers are violet-blue with dark pink eye marks and with a small notch and the tips of the petals, and just before dropping petal centers lighten to white and marks in eye fade away. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Rocky Road Violet Blue'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 1, 2019. Subsequently, the new plant was advertised in the "Walters Gardens 19-20 Catalog" by Walters Gardens, Inc. released on May 29, 2019. The claimed plant was first sold on Jul. 8, 2019 by Walters Gardens, Inc., who obtained the plant and all information relating thereto, from the inventor. No plants of *Phlox* 'Rocky Road Violet Blue' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant known as *Phlox* 'Rocky Road Violet Blue' and will be referred to hereafter by its cultivar name, 'Rocky Road Violet Blue', or the "new plant". The new plant was hybridized by the inventor at a wholesale perennial nursery in Zeeland, Mich. on May 1, 2015 as a cross between *Phlox subulata* 'Purple Beauty' (not patented) as the female or seed parent and *Phlox kelseyi* 'Lemhi Purple' (not patented) as the male or pollen parent. The new plant passed initial evaluation on the spring of 2017 and was assigned the breeder code 15-42-2 through the remaining evaluation process. 'Rocky Road Violet Blue' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Rocky Road Violet Blue' is unique from all other Hybrid Spring *Phlox* known to the inventor. The nearest comparison plants known to the inventor include: the female and male parents, 'Rocky Road Grape' U.S. Plant patent application Ser. No. 16/873,085, 'Rocky Road Magenta' U.S. Plant patent application Ser. No. 16/350,916, 'Violet Pinwheels' U.S. Plant Pat. No. 25,884, 'Rocky Road Periwinkle' U.S. Plant patent application Ser. No. 16/873,084 and 'Plumtastic' U.S. Plant Pat. No. 28,896. 'Purple Beauty' has a larger more spreading habit and the flowers are purple with a dark violet-purple eye and moderately notched apices. 'Lemhi Purple' has a slightly taller habit with deeper purple-violet flowers without darker purple marks near center eye and without notches at the petal apices. 'Rocky Road Grape' has flowers that reddish purple with a small dark purple eye and more deeply notched petal apices. 'Rocky Road Magenta' has vibrant magenta-purple flowers with small dark-purple eye marking and without a notched petal apex. 'Violet Pinwheels' has shorter height with violet-blue flower color with more cupped corolla and more deeply cleft petal apices. 'Rocky Road Periwinkle' has periwinkle-blue flowers. 'Plumtastic' has flowers of violet-pink with purple markings near the eye, and the flower initially has a light, near-white center that darkens to the same violet-pink at maturity.

*Phlox* 'Rocky Road Violet Blue' differs from and all other *Phlox* known to the inventor in the following repeatedly observed traits in combination:

1. Vigorous plants of dense spreading habit, spreading by rooting stems, producing short, clean, puberulent, bright-green, linear leaves;
2. Multiple heavily-branched stems produce branched panicles;
3. Flower beginning in mid-April and continuing for up to five weeks, in cool conditions, completely covering plant at peak flowering;
4. Flowers of violet-blue with dark pink eye and with small notches at the tip of the petals;
5. Plant is able to withstand dry conditions once established.

BRIEF DESCRIPTION OF THE DRAWINGS

The photographs of the new plant demonstrate the unique traits of *Phlox* 'Rocky Road Violet Blue' and the overall appearance of the plant at three-years-old growing in a full-sun trial beds in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
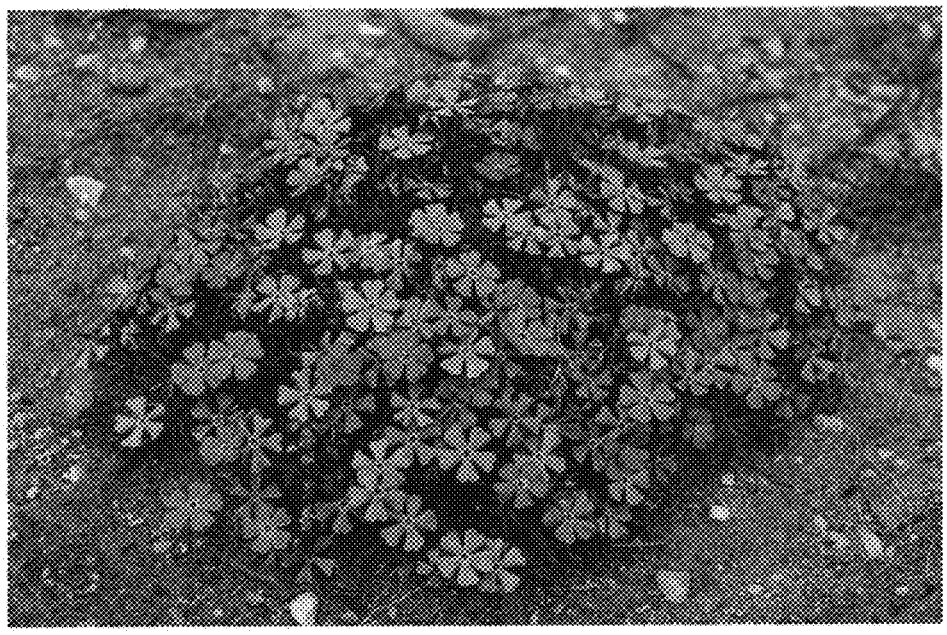
FIG. 1 shows a landscape habit view of the new plant in peak flower.
Figure 2:
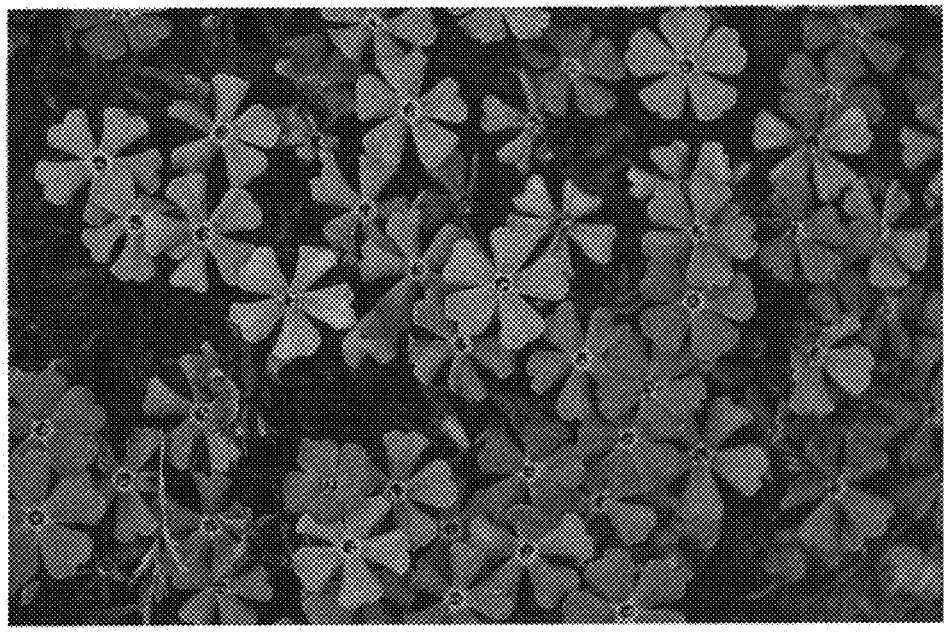
FIG. 2 shows a close-up of the flowers and buds.

The following descriptions and color references are based on the 2015 edition of The Royal Horticultural Society Colour Chart except where common dictionary terms are used. *Phlox* 'Rocky Road Violet Blue' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox subulata* 'Purple Beauty', male or pollen parent is *Phlox kelseyi* 'Lemhi Purple';

Plant habit: Winter-hardy, evergreen herbaceous perennial; short, dense, producing about 40 to 65 stiff, highly-branched prostrate stems; foliage 7.0 cm tall and 43.5 cm wide, average 6.0 cm tall and 41.0 cm wide; flowering to 9.0 cm tall and 45.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear to subulate; apex narrowly acute to mucronulate; base truncate, clasping; margin entire; glabrous both adaxial and abaxial; about 19.0 mm long by about 4.5 mm wide, average about 16.5 mm long and 3.5 mm wide;

Leaf color: Adaxial expanding and mature nearest RHS 137A, abaxial both expanding and mature between RHS 138A and RHS 138B;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; prostrate; highly branching; to about 5.0 mm long and 1.0 mm diameter near base;

Stem color: Color nearest RHS 145A when exposed;

Nodes: Proximally about 5.0 mm apart; distally less than 1.0 mm apart;

Node color: Color nearest RHS 145C;

Inflorescence: Upright to outwardly; about 2.5 cm long and 3.0 cm wide; average of 3 flowers;

Flowers: Perfect; salverform; mostly flat faced; about 19.0 mm across face and 13.0 mm long; with fused corolla tube about 12.0 mm long and 2.0 mm diameter near face; attitude upright to outwardly;

Flower longevity: About 5 days on plant; self-cleaning;

Flower fragrance: Not detected;

Buds one to two days prior to opening: Narrowly oblanceolate, to narrowly clavate; bluntly acute apex with rounded base; petals implicate; about 17.0 mm long, 5.5 mm long in terminal bulb portion and 9.5 mm long in tube; corolla tube to 2.0 mm diameter, bulb to 5.5 mm diameter;

Bud color: Exposed petal bulb portion nearest RHS 92B; between tube and bulb nearest RHS 103A, corolla tube basal 2.0 mm nearest RHS 145C and distal tube nearest RHS 85D; calyx nearest RHS 137B with strong blush in high light exposure of nearest RHS N187A;

Petals: Five; consisting of limb and basal claw fused into corolla tube; apex rounded and sharply and shallowly cleft to about 0.5 mm deep; limbs not imbricate; margin entire; glabrous adaxial and abaxial;

Petal size: Limb about 9.0 mm long and 8.0 mm wide near middle; tube about 12.0 mm long and 2.0 mm diameter;

Petal color upon opening:

*Adaxial*.—Limb nearest RHS N87B with splashed ring near eye about 1.0 mm long and wide nearest RHS 93A and central eye about 1.0 mm wide nearest RHS NN155C; proximal 4.0 mm of tube nearest RHS 145C, remaining distal tube portion nearest RHS 91A.

*Abaxial*.—Limb nearest RHS 90D, proximal 1.0 mm of tube nearest RHS 145A, next proximal 2.0 mm nearest RHS 150D, remaining distal tube portion between RHS 91B and RHS 91C.

Petal color upon maturity:

*Adaxial*.—Adaxial: limb nearest RHS N81B near center and nearest RHS N87C in the perimeter one-half, with splashed ring faded to match center eye nearest RHS NN155C; proximal 4.0 mm of tube nearest RHS 145C, remaining distal tube portion nearest RHS 91A.

*Abaxial*.—Limb nearest RHS 90D, proximal 1.0 mm of tube nearest RHS 145A, next proximal 2.0 mm nearest RHS 150D, remaining distal tube portion between RHS 91B and RHS 91C.

*Androecium*.—Typically five.

Filaments: Typically five, adnate to inner corolla to various heights about 7.0 mm to 11.0 mm from base; free in the distal 1.0 mm to 2.0 mm long and 0.2 mm in diameter; color nearest RHS NN155D;

Anther: Five; oblong elliptic; basifixed; oblong, about 2.5 mm long by 1.0 mm wide; color nearest RHS 17C;

Pollen: Nearly microscopic; color nearest RHS 23A;

Gynoecium: One pistil per flower; 12.0 mm long;

Style: Cylindrical; about 9.0 mm long and 0.3 mm diameter when flower is mature; persistent after flower abscission; color nearest RHS 145D;

Stigma: Trifid in proximal 1.5 mm long, about 0.3 mm diameter; color nearest RHS 9B;

Ovary: Inferior; conical; glabrous; acute apex and truncate base; about 1.5 mm long and 1.0 mm diameter; color nearest RHS 143A;

Calyx: Campanulate; pubescent abaxial, glabrous adaxial; about 7.0 mm long and 3.5 mm across at apex;

Sepals: Five; lanceolate; glabrous adaxial and puberulent abaxial; narrowly acute apex, fused in basal 4.0 mm; margin entire; matte abaxial, and lustrous adaxial; individually about 7.0 mm long and 1.0 mm wide at fusion;

Sepal color: Adaxial nearest RHS 137A in dorsal region; abaxial nearest RHS 137B with strong blush in high light exposure of nearest RHS N187A;

Peduncle: Glabrous; strong, flexible; mostly upright; cylindrical; to about 1.5 mm diameter at base and 2.5 cm long;

Peduncle color: Low light or ventrally nearest RHS 146C; high light or ventrally nearest RHS 146C with weak to moderate blush nearest RHS 187A;

Pedicle: Cylindrical; glabrous; flexible; upright to outwardly; variable lengths from about 7.0 mm to 5.0 mm long and 0.7 mm diameter;

Pedicle color: Variable depending on light exposure; with low light or ventrally nearest RHS 146D; high light or dorsally nearest RHS 146C with strong blush to solid RHS 187A; Fruit and seeds: not observed;

Hardiness and culture: The new plant grows best with full sun, light moisture and deep drainage; hardy to at least from USDA zone 4 through 8.

Disease and pest resistance: *Phlox* 'Rocky Road Soft Violet Blue' demonstrates excellent powdery mildew resistance under conditions that would normally show symptoms.

I claim:

1. A new and distinct cultivar of Hybrid Creeping *Phlox, Phlox* plant named 'Rocky Road Violet Blue', as herein described and illustrated.

* * * * *